(12) United States Patent
Verma et al.

(10) Patent No.: US 8,585,703 B2
(45) Date of Patent: *Nov. 19, 2013

(54) ADJUSTMENT TOOL FOR EXTERNAL FIXATOR

(75) Inventors: Umesh Verma, Delhi (IN); Klaus Dorawa, Safnem (CH); Usha Mathur, New Delhi (IN)

(73) Assignee: Stryker Trauma SA (CH)

( * ) Notice: Subject to any disclaimer, the term of this patent is extended or adjusted under 35 U.S.C. 154(b) by 65 days.

This patent is subject to a terminal disclaimer.

(21) Appl. No.: 13/302,516

(22) Filed: Nov. 22, 2011

(65) Prior Publication Data

US 2012/0150180 A1 Jun. 14, 2012

(30) Foreign Application Priority Data

Dec. 9, 2010 (EP) .................................... 10194328

(51) Int. Cl.
*A61B 17/00* (2006.01)

(52) U.S. Cl.
USPC .......................................................... 606/59

(58) Field of Classification Search
USPC ............... 606/54–59; 403/384, 385, 395, 289
See application file for complete search history.

(56) References Cited

U.S. PATENT DOCUMENTS

| | | | | |
|---|---|---|---|---|
| 3,961,854 A | * | 6/1976 | Jaquet | 403/59 |
| 5,304,177 A | * | 4/1994 | Pennig | 606/58 |
| 5,810,814 A | * | 9/1998 | Newson | 606/59 |
| 7,261,713 B2 | * | 8/2007 | Langmaid et al. | 606/59 |
| 2007/0123858 A1 | * | 5/2007 | Strub et al. | 606/54 |
| 2012/0150180 A1 | | 6/2012 | Verma et al. | |

FOREIGN PATENT DOCUMENTS

FR 2698534 A1 6/1994

OTHER PUBLICATIONS

European Search Report dated Mar. 8, 2011 for EP 10194328.0.

* cited by examiner

*Primary Examiner* — Pedro Philogene
(74) *Attorney, Agent, or Firm* — Lerner, David, Littenberg, Krumholz & Mentlik, LLP

(57) ABSTRACT

An adjustment tool for an external fixator comprises a fitting element for holding fast a clamping assembly of the external fixator. A positioning clamp is provided for fixing the adjustment tool on a rod of the external fixator near the clamping assembly. A connecting element is attached to the fitting element and the positioning clamp is adapted to move the fitting element towards to or away from the positioning clamp. The fitting element comprises a blocking sleeve adapted to push the uppermost jaw of the clamping assembly in the direction of the longitudinal axis of the clamping assembly to block the second upper most jaw against an abutment portion of the fitting element. The tool further comprises an actuation element within the blocking sleeve to actuate the locking element of the clamping assembly for releasing the rod within the clamping assembly without releasing the bone pin.

10 Claims, 3 Drawing Sheets

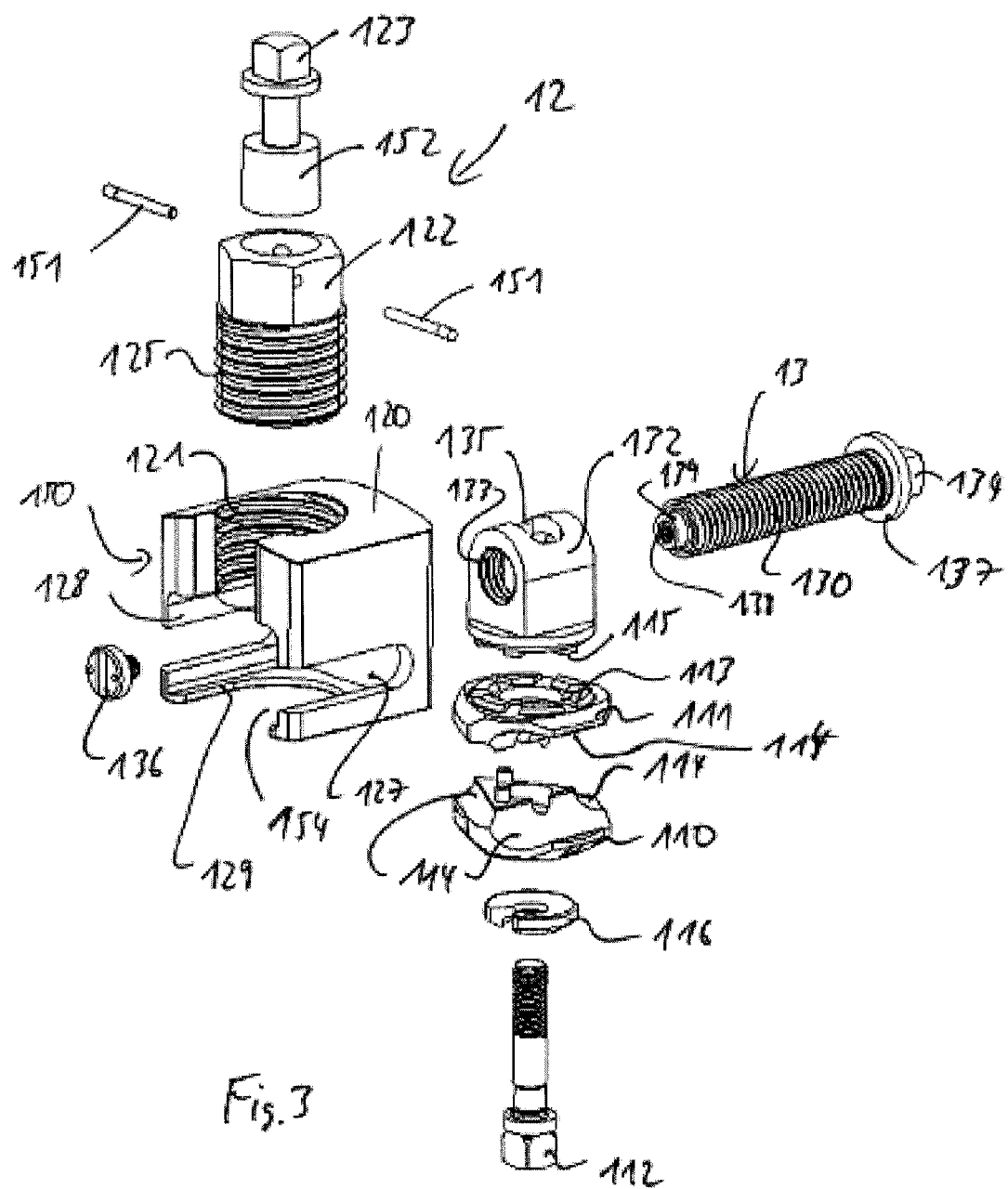

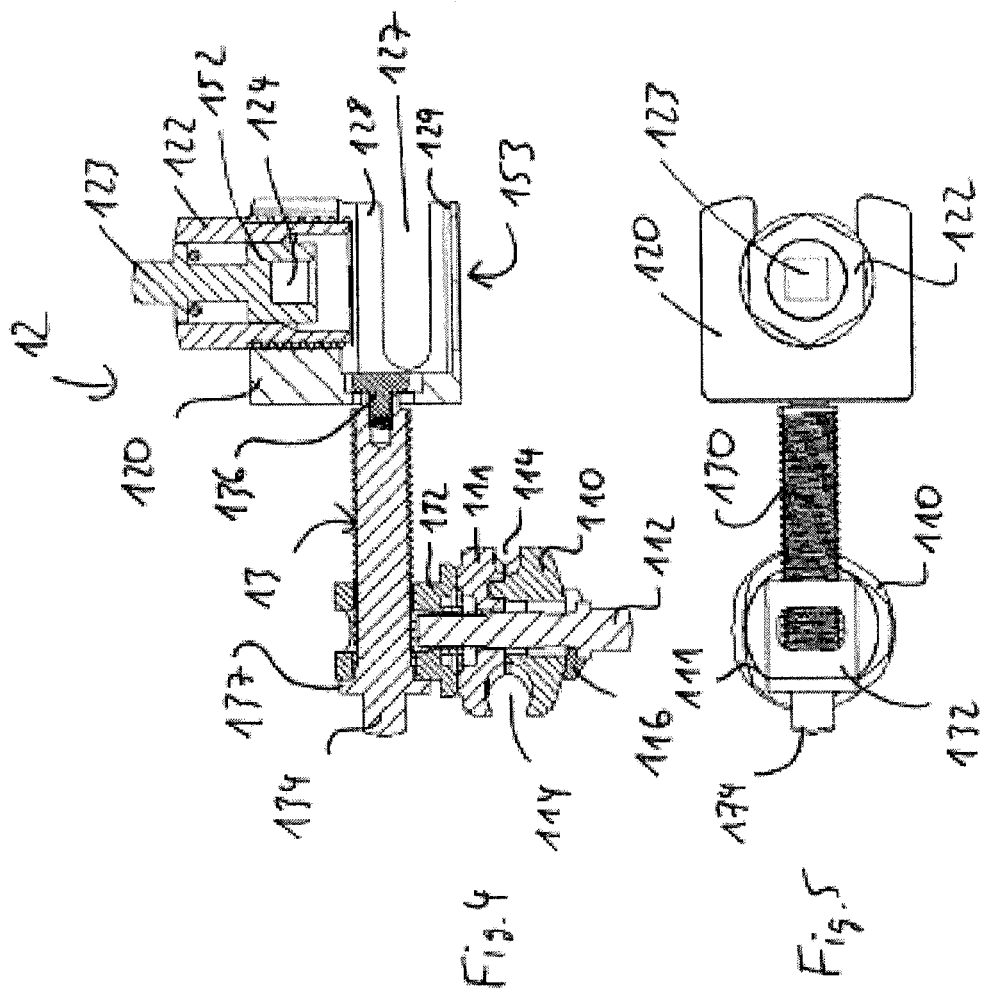

ADJUSTMENT TOOL FOR EXTERNAL FIXATOR

CROSS-REFERENCE TO RELATED APPLICATION

The present application claims priority from European Patent Application No. 10 194 328.0 filed Dec. 9, 2010, the disclosure of which is hereby incorporated herein by reference.

BACKGROUND OF THE INVENTION

The present invention relates to an adjustment tool for an external fixator adapted for securing a first bone portion in a position relative to a second bone portion, wherein the adjustment can comprise a compression or a distraction.

An external fixator in use with a patient is usually a device comprising at least two clamping assemblies for receiving at least one bone pin each. In a preferred embodiment, each clamping assembly comprises a second clamp for receiving a rod of an external fixator which extends over the fracture. If a compression or a distraction is to be applied, at least one clamping assembly has to be loosened with the risk that the angular orientation of the corresponding bone pin engaging the bone from one side of the fracture loses its orientation.

U.S. Pat. No. 5,304,177 discloses an integrated adjustable fixator having two clamping assemblies within which each receives a bone pin to be entered into a bone of a patient of on each side of a fracture. Between the two clamping assembling holding the bone pins there is provided a main body having a worm in order to vary the distance between the two clamping assemblies. The device allows adjusting the distance between such two bone pins and therefore can be considered as a compression and/or distraction tool itself.

U.S. Pat. No. 7,261,713 discloses another bone fixator which is adjustable, wherein two multipin clamping assemblies are attached to a longitudinal main body. The main body allows different orientations of the clamping bodies and comprises a longitudinal translation element which allows shifting the positions of the two multipin clamping assemblies.

The prior art allows an easier adaptation of the distance between the clamping assemblies providing bone pins on each side of a fracture in a bone of a patient but they fail to provide a rigid frame. The existence of pivoting joints between the clamping assemblies necessitates some forces to block the universal joints.

SUMMARY OF THE INVENTION

Based on this prior art it is one aspect of the present invention to provide a compression and distraction tool allowing a more secure and easy variation of the distance of such two bone pins of an external fixator.

It is a further aspect of the invention to provide a compression and distraction tool which can be used with a variety of clamping assemblies.

A further aspect of the invention is to provide a compression and distraction tool which is not part of the external fixator, i.e. which is only used when the length variation is to be adjusted but is not part of the external fixator which is, e.g. worn by a person having a broken limb.

The adjustment tool is to be used for an external fixator for exerting a compression or distraction on a broken bone fixed by bone pins spanned over such a fracture. Therefore the adjustment tool comprises:

a fitting element for holding fast a clamping assembly of the external fixator,
a positioning clamp for fixing the adjustment tool on a road of the external fixator near said clamping assembly, and
a connecting element attached to the fitting element and the positioning clamp, adapted to move the fitting element towards to or away from the positioning clamp.

Thereby the fitting element comprises a blocking sleeve adapted to push the uppermost jaw of the clamping assembly of the external fixator in the direction of the longitudinal axis of the clamping assembly to block the second upper most jaw against an abutment portion of the fitting element and an actuation element within the blocking sleeve to FIG. 4 shows a section of the compression tool according to FIG. 3, and actuate the locking element of the clamping assembly for releasing the rod of the external fixator within the clamping assembly without releasing the bone pin.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 3 shows an exploded view of the compression tool according to FIG. 1;

FIG. 4 shows a section of the compression tool according to FIG. 3; and

FIG. 5 shows a view from above on the compression tool according to FIG. 3.

DETAILED DESCRIPTION

Figure 1:
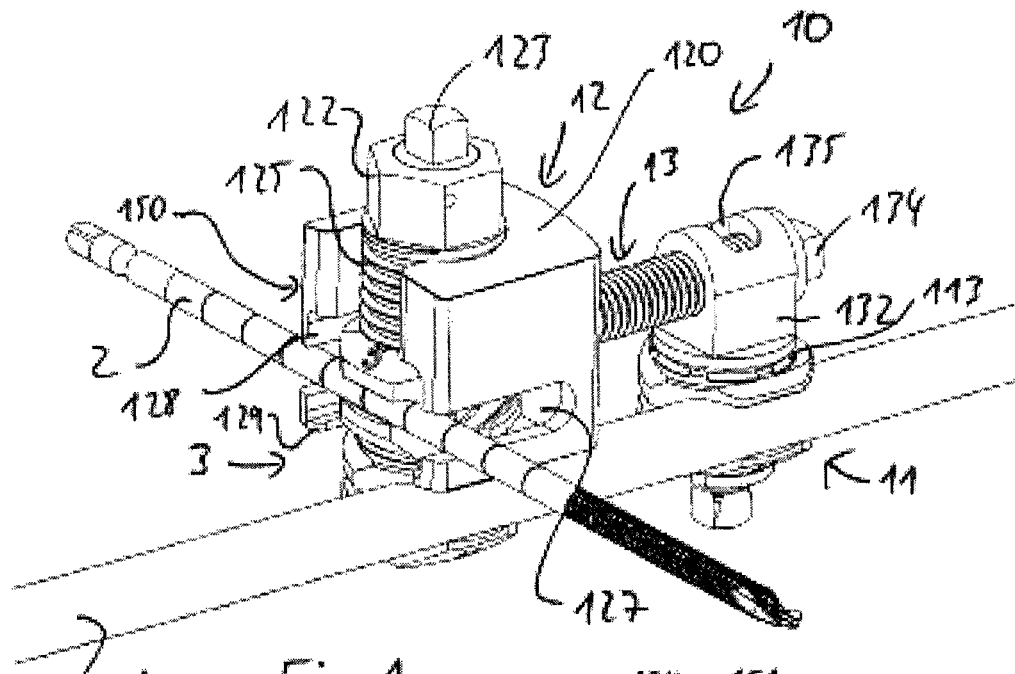
FIG. 1 shows a perspective view of the device according to the invention in connection with one clamping assembly, one rod and one bone pin.

FIG. 1 shows a perspective view of the compression tool 10 used with an external fixator and shows some parts of such an external fixator but not the entire fixator which may be similar to that shown in U.S. Pat. No. 6,080,153. Throughout the following specification tool 10 is always mentioned as a compression tool, since compression of a fracture is the most common adjustment of the distance between two bone pins over a fracture, but the tool is also usable as a distraction tool, since the distance between such bone pins can also be enlarged. The tool is therefore in fact a combined compression and distraction tool i.e., an adjustment tool.

The external fixator for which the tool 10 is intended to be used with comprises a first clamping assembly, which is not shown in the drawings. The first clamping assembly to attach a bone pin on one side of the fracture of a limb is then connected with rod 1 to span over the fracture. On the other side of the fracture a second clamping assembly 3 is attached to rod 1 and comprises a second bone pin 2 which is intended to be entered into the bone on the other side of the fracture in view of the above mentioned bone pin in connection with the first clamping assembly of the external fixator, which is not shown in the drawings. Clamping assembly 3 has several elements which are shown in the cross-section of FIG. 2. The second clamping assembly 3 is a clamping assembly according to co-pending U.S. Patent Application Publication No. 2010/0298827 assigned to the assignee of the present invention. It can also be a clamping assembly according to U.S. Pat. No. 6,080,153.

In any case it has two pairs of jaw, a lower pair of jaws 30 and 31 providing recesses or receptions 36 to accommodate rods 1 and pins 2. A further upper pair of jaws 32 and 33 also comprises recess or reception 36 to accommodate rods 1 and pins 2. The pairs of jaws 30, 31, 32 and 33 are connected with a connection screw 34 which is actuated through head 35. Screw 34 extends along the longitudinal axis of the second clamping assembly 3. Such a clamping assembly 3 is also known from U.S. Pat. No. 6,080,153 having a similar design. In this context it is only important that the clamping assembly has at least two pairs of jaws 30, 31, 32, 33 allowing accommodating a rod 1 and a bone pin 2 at the same time. They are embodiments on the market within which the middle jaws 31 and 32 can be replaced by one single jaw. It is preferred that there are different receptions 36 or inserts to adapt the receptions 36 at different levels in height in view of the rods 1 and pins 2 which should not be positioned at the same level.

The outer form of such a clamping assembly 3 is usually cylindrical or nearly cylindrical. However in a view from above it can also have a square or rectangular cross-section. As mentioned above first and second clamping assemblies are used to fix two or more bone pins 2 on two sides of a fracture, wherein a rod 1 is used to establish a rigid frame and a defined distance, position and orientation of the bone pins 2.

During the use of such an external fixator it is now contemplated that the two fractured bone parts have to be displaced one in the direction towards the other (i.e. a compression movement) or they have to be displaced in the opposite direction (i.e. a distraction). According to prior art solutions a worm bridging the clamping assemblies has to be actuated to vary the distance.

In the present context having a rigid and fixed rod 1 giving a higher strength to the external fixator, such a compression or distraction would not be possible without loosening the actuator screw 34 through turning the head 35. However, this not only enables gliding of the lower jaws 30 and 31 along the rod 1 but also opens the clamping jaws 32 and 33 holding the bone pin 2.

According to the invention it is suggested to use compression tool 10 as follows:

As it can be seen in FIGS. 1 to 5 compression tool 10 comprises a positioning clamp 11, adapted to be clamped on rod 1, a connection element 13, connecting the positioning clamp 11 with the fitting element 12 which is adapted to hold fast the clamping assembly 3.

The positioning clamp 11 comprises a lower jaw 110 and an upper jaw 111 providing receptions 114. In the embodiment shown in the figures there are three receptions or cavities 114 of different sizes. It is important that one reception 114 is adapted to accommodate rod 1. Through actuating the longitudinal screw 112 against the washer 116 jaws 110 and 111 are closed and clamp rod 1. Screw 112 extends beyond jaw 111 into the connection body 132 of the connecting element 13.

In a simple embodiment it would be possible to combine jaw 111 and connecting body 132 in one single element. However it is preferred to have two different elements to have a lower structured surface 113 on jaw 111 and a complementary structured surface on the complementary connecting body 132. This enables turning the jaws 110 and 111 around the longitudinal axis of screw 112, thus choosing the reception 114 of corresponding size to accommodate rod 1.

The connecting body 132 has a through bore having an inner thread 133 which is orientated perpendicular to the axis of the above mentioned fixing screw 112 of positioning clamp 11. The connection body 132 also has an upper opening 135 in the vicinity of the longitudinal axis of screw 112.

The connecting element 13 comprises a worm 130 having an outer thread adapted to be rotated in the bore of the connecting body 132 comprising an inner thread 133. The worm 130 has a flange 137 and a turning knob 134 at one end. It is not necessary that the bore of the connecting body 132 separated into two parts on both sides of upper opening 135 has a complementary inner thread 133. In the embodiment shown in FIG. 2 it can be seen that the bore adjacent to flange 137 has no inner thread.

On the other side of the worm 130 it has a central bore 138 and a thread-free cylindrical sleeve 139 of smaller diameter intended to be introduced and to make the connection with the casing 120 of the fitting element 12. The casing 120 of the fitting element 12 has—in a view form above—the form of the letter C, wherein the closed portion of the fitting element is oriented towards the connecting body 132. The casing 120 has a bore to accommodate the complementary sleeve 139 of worm 130. The worm 130 is fixed within said bore with the counter screw 136 to allow rotation of worm 130. Counter screw 136 has a larger head than the bore within casing 120. It is thus clear that rotation of worm 130 changes the position of connection body 132 between the casing 120 and the flange 137 of worm 130. The fixed relationship between counter screw 136 and worm 130 can be especially achieved through gluing or it can be blocked by using a pin or welding etc.

The fitting element 12 comprises beside casing 120 which is in a fixed rotational relationship with worm 130 a blocking sleeve 122 having an outer thread 125 being complementary to an inner thread 121 of casing 120 which is located near the top of the casing 120. Within blocking sleeve 122 there is provided an actuation screw 123 having a hollow cylinder 152 with a reception hole 124 at its lower end. Hollow cylinder 152 is complementary for a positive fit to accommodate head 35 of the clamping assembly for which it is the adjustment tool.

Casing 120 further comprises a transverse slit 127 being at right angles to the longitudinal axis of blocking sleeve 122. The port of the transverse slit 127 is on the side of the open end of the "C" in the lower portion of the connecting casing 120 below inner thread 121. Below the transverse slit 127—on both sides of the open "C"—there is provided a lower shoulder 129 protruding into the lower reception opening 154 and providing a flange on the lower end of the casing 120. As mentioned above the C-form of the sleeve comprises a lower reception opening 154 opposite to the inner thread 121. On the other side of the lower shoulder 129 near the inner thread there is provided a further reception shoulder 128 protruding into the opening partially filled by the blocking sleeve 122 from above.

Figure 2:
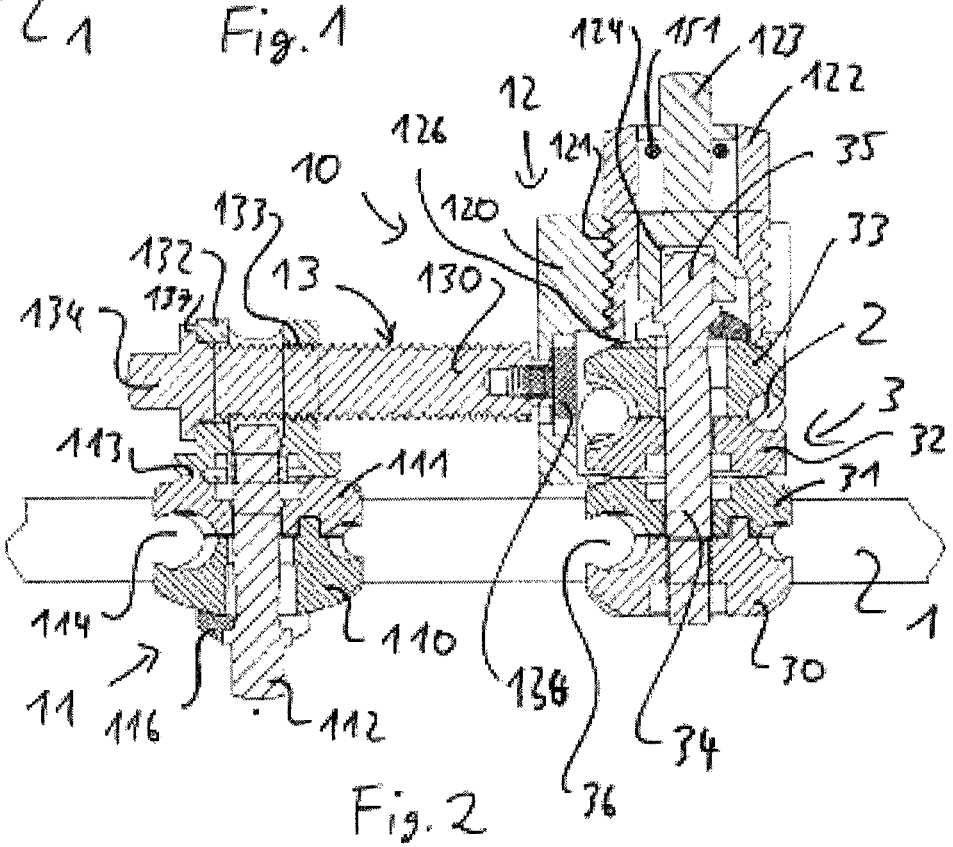
FIG. 2 shows a partial cross-section of FIG. 1 along the middle axis of the extension element.

The function of the device is therefore as follows. Two bone pins from which only one bone pin 2 is shown in FIG. 1 or 2 are lodged in the bone of a patient on both sides of a fracture. The rod 1 spans the fracture and is connected to the bone pins 2 on both sides through two clamping assemblies 3. In order to move one bone pin 3 in the direction of the longitudinal axis of the underlying rod 1, either compressing or distracting the fracture region, one of the clamping assemblies 3 is to be moved and there the use of the adjustment tool 10 is shown in FIGS. 1 and 2. The two jaws 30 and 31 of the clamping assembly 3 of the external fixator clamp the rod and the two jaws 32 and 33 of the clamping assembly 3 hold the bone pin 2.

The adjustment tool 10 is presented with the open "C", i.e. from the lateral opening 150 towards the upper two jaws 32 and 33 of the clamping assembly 3. The fitting element 12 is pushed over the upper two jaws 32 and 33 so that these are located between the upper and lower shoulders 128, 129. The bone pin 2 is therewith lodged within the lateral slit 127, wherein the length of the slit permits different orientations of the bone pin 2 in the horizontal axis; it is not necessary that the bone pin 2 is perpendicular to rod 1 as shown in FIG. 1. The orientation of bone pin 1 depends on the position of the upper jaws 32, 33 (more particularly the reception 36 receiving the bone pin 2) in relationship to the position of the lower jaws 30, 31 (more particularly the reception 36 receiving the rod 1).

When the upper portion of the clamping assembly 3 is within the casing 120 of the fitting element 12, then the blocking sleeve 122 is rotated through action of the threads 121, 125 down onto the head 135 of the clamping assembly 3. This allows introducing the head 35 into the reception hole 124 of the blocking sleeve 122. When there is a positive fit through pushing the blocking sleeve 122 down on the upper jaw 33, where the underside 126 of the blocking sleeve 122 contacts said upper jaw 33, then the fitting element 12 is fixed to the clamping assembly 3 of the external fixator.

Then, subsequently, the positioning clamp 11 is also attached to rod 1 through jaws 110, 111 by actuation of screw 112. Then positioning clamp 11 and fitting element 12 with the clamping assembly 3 are securely fixed to the rod 1. When said fitted clamping assembly 3 and positioning assembly 11 are now fixed on the rod 1, then the head of worm 134 is turned until a force would be exercised on positioning clamp 11 and fitting element 12 by worm 130 which can be detected by the user of the adjustment tool.

After this moment actuation head 123 is turned to loosening the clamping assembly 3. Since jaw 32 is pushed against the lower shoulder 129, the opening of screw 34 does not liberate the bone pin 2, which is still pinched through the pressure of the underside 126 on the upper jaw and the abutment action of the lower shoulder 129; but only opens the lower jaws 30 and 31 in order to release rod 1 allowing a movement of the clamping assembly 3 as a whole in the direction of the axis of rod 1.

This can be effected through turning the worm head 134 so that rotation of worm 130 in the connection body 132 pulls the fitting element 12 with the clamping assembly 3 being in a positive fit within the fitting element 12. This pulling action is acting in direction of the positioning clamp 11. Of course the head 134 can also be rotated in the opposite position thus pushing the fitting element 12 with the clamping assembly 3 away from the positioning clamp 11. The kind of motion, i.e. distraction or compression, depends on the side where the positioning clamp 11 is fixed on the rod, either between the two clamping assemblies 3 or on the opposite side.

The displacement of the one bone pin 2 in the direction of the longitudinal axis of the underlying rod 1 is equivalent to a movement of the worm 130 towards the head 134 of the worm 130.

The embodiment of the fitting element 12 shows the lateral opening 150 opposite to the positioning bore of the worm 130. In other embodiment it is possible to provide the opening in an 90 degree angle to the worm 130 thus allowing to open the "C" not in the direction of the distraction or compression movement. However then the pin 3 has to be accommodated at a different level, e.g. lower than the worm 130.

In a different motorized embodiment not shown in the drawings, the fitting element 12 and the connecting element 13 can be combined in one single servo-motor assembly providing the same longitudinal displacement as in the embodiment of the drawings. Such a servo-motor assembly would have a fixed connection with the casing 120 and would provide or have a fix connection with the upper structured surface 115. In fact the servo-motor assembly replaces the worm in the embodiment shown in the drawings. In other words, the connecting element 13 comprises an extendable element connected to the fitting element 12 and being in a fixable connection with the positioning clamp 11 allowing thus a translatory movement between the fitting element and the positioning clamp 11, acting as a. mechanical translation means.

It is preferred that the positioning clamp 11 is in a fixable connection with the connecting element 13 and not in a fixed connection. A fixable connection allows e.g. a rotation of the positioning clamp 11 and their receptions 114 around an axis.

Pins 151 allow maintaining the hollow cylinder 152 inside and the actuation head 123 outside the blocking head 122. It would also be possible to use a different blocking means allowing a longitudinal movement of the hollow cylinder to come into engagement with the screw head 35. In principle it could also be allowed that the element 123/152 can be dissociated from the blocking sleeve 122.

It is clear for someone skilled in the art that the interior cross-section of the blocking sleeve 122 as well as the shoulders 129 as well as the reception 128 has to be adapted to the specific clamping assembly 3. However, it is also clear, that any clamping assembly intended to be used for a rod-to-rod or rod-to-pin coupling can be used in such a structure to block the second upper most jaw of the clamp against an abutment portion of the fitting element, wherein the actuation element within the blocking sleeve is provided to actuate the locking element of the clamping assembly for releasing the rod of the external fixator within the clamping assembly without releasing the bone pin.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An adjustment tool for an external fixator comprising a clamping assembly having two sets of jaws, the adjustment tool comprising:
    a first and second pair of jaws, each pair of jaws having first and second jaw members defining a first and a second cavity for respectively receiving a bone pin and a rod of the external fixator;
    a fitting element having a slotted opening for receiving the first jaw member and having a first surface for contacting a surface of the first jaw of the first pair of jaws, a locking sleeve mounted on the fitting element for movement towards the first surface thereon and into engagement with a surface of the second jaw of the first pair of jaws for moving the second jaw towards the first jaw;
    a locking element extending through the first and second pair of jaws for moving the first jaw of the first and second pair of jaws towards the second jaw, the locking element independently operable from the locking sleeve.

2. An adjustment tool for an external fixator as set forth in claim 1 further comprising:
    a positioning clamp for fixing the adjustment tool on a rod of the external fixator adjacent the clamping assembly, and
    a connecting element attached to the fitting element and the positioning clamp adapted to move the fitting element towards to or away from the positioning clamp, wherein the positioning clamp comprises a pair of jaws providing at least one reception to accommodate a rod of an external fixator.

3. The adjustment tool according to claim 2, wherein the positioning clamp comprises a structured surface and wherein the connecting element comprises a complementary structured surface allowing a rotation of the connecting element against the positioning clamp around an axis provided by the longitudinal axis of the positioning clamp.

4. The adjustment tool according to claim 2, wherein the connecting element comprises an extendable element connected to the fitting element and being in a fixable connection with the positioning clamp allowing thus a translatory movement between the fitting element and the positioning clamp.

5. The adjustment tool according to claim 2, wherein the connecting element comprises a worm being rotatably fixed within the fitting element and a connecting casing to accommodate the worm, wherein the connecting casing comprises an inner thread complementary to the thread of the worm allowing a translatory movement between the fitting element and the positioning clamp being in a fixable connection with the connecting element.

6. The adjustment tool according to claim 2, wherein the connecting element comprises a servo motor fixedly connected to the fitting element and being in a fixable connection with the positioning clamp allowing a translatory movement between the fitting element and the positioning clamp.

7. The adjustment tool according to claim 2, wherein the fitting element comprises a lateral opening to receive the upper jaws holding a bone pin of an external fixator between the blocking sleeve and the abutment portion, the lateral opening being parallel to said longitudinal axis of the clamping assembly of the external fixator to be introduced into the lateral opening.

8. The adjustment tool according to claim 7, wherein the fitting element comprises a transverse opening to accommodate said bone pin of an external fixator, the transverse opening being transverse to said longitudinal axis of the clamping assembly of the external fixator to be introduced into the lateral opening.

9. The adjustment tool according to claim 7, wherein the blocking sleeve comprises an outer thread, being complementary to an inner thread within a casing of the fitting element to move the blocking sleeve in the direction of said longitudinal axis, and a blocking underside complementary to the upper surface of the upper jaw of the clamping assembly, wherein the abutment portion of the fitting element is a protruding flange into the lower reception opening.

10. The adjustment tool according to claim 7, wherein the actuation element of the blocking sleeve is an inner rotatable shaft having a reception for receiving the actuation head of the locking element of the clamping assembly for releasing the rod of the external fixator.

* * * * *